United States Patent [19]

Schneiderman

[11] Patent Number: 5,046,503
[45] Date of Patent: Sep. 10, 1991

[54] ANGIOPLASTY AUTOPERFUSION CATHETER FLOW MEASUREMENT METHOD AND APPARATUS

[75] Inventor: Gary Schneiderman, Walnut Creek, Calif.

[73] Assignee: Advanced Cardiovascular Systems, Inc., Santa Clara, Calif.

[21] Appl. No.: 343,426

[22] Filed: Apr. 26, 1989

[51] Int. Cl.⁵ .................... A61B 5/02; A61B 8/06; A61M 25/00
[52] U.S. Cl. .................... 128/692; 606/194; 128/662.06; 604/96; 604/102
[58] Field of Search .................... 128/662.06, 691, 692, 128/693

[56] References Cited

U.S. PATENT DOCUMENTS

| | | | |
|---|---|---|---|
| 4,665,925 | 5/1987 | Millar | 128/663 |
| 4,852,580 | 8/1989 | Wood | 128/693 |
| 4,873,989 | 10/1989 | Einzig | 128/692 |
| 4,877,031 | 10/1989 | Conway et al. | 606/194 |
| 4,889,128 | 12/1989 | Millar | 126/662.06 |
| 4,944,745 | 7/1990 | Sogand et al. | 604/46 X |

*Primary Examiner*—Francis Jaworski
*Attorney, Agent, or Firm*—Fulwider, Patton, Lee & Utecht

[57] ABSTRACT

An angioplasty autoperfusion catheter flow measurement apparatus includes a balloon catheter having an autoperfusion lumen incorporated therein which is acoustically in communication with a flow velocity measuring system. The flow measuring system may include a Doppler transducer, usually a section of piezoelectric material, located adjacent to the autoperfusion lumen and connected to an external activating and measuring device that indicates the velocity of the blood flowing through the autoperfusion lumen at a remote location outside the patient's body.

26 Claims, 2 Drawing Sheets

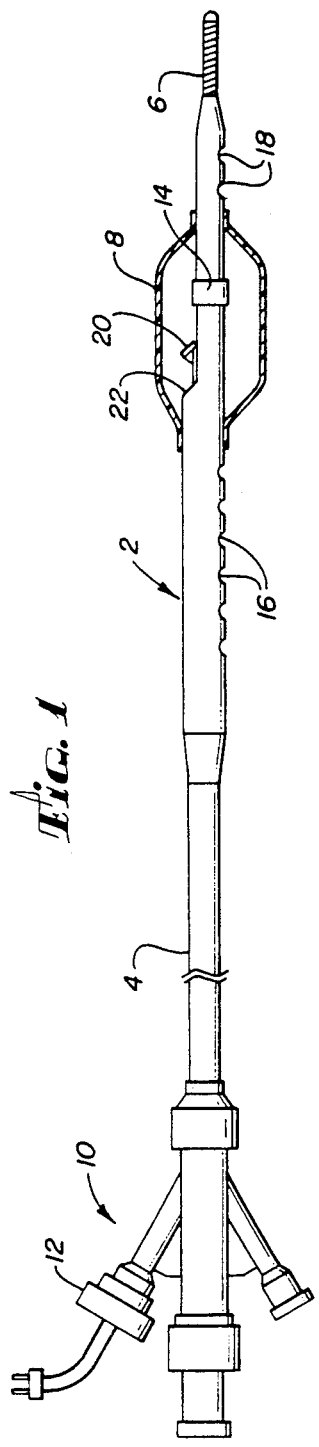
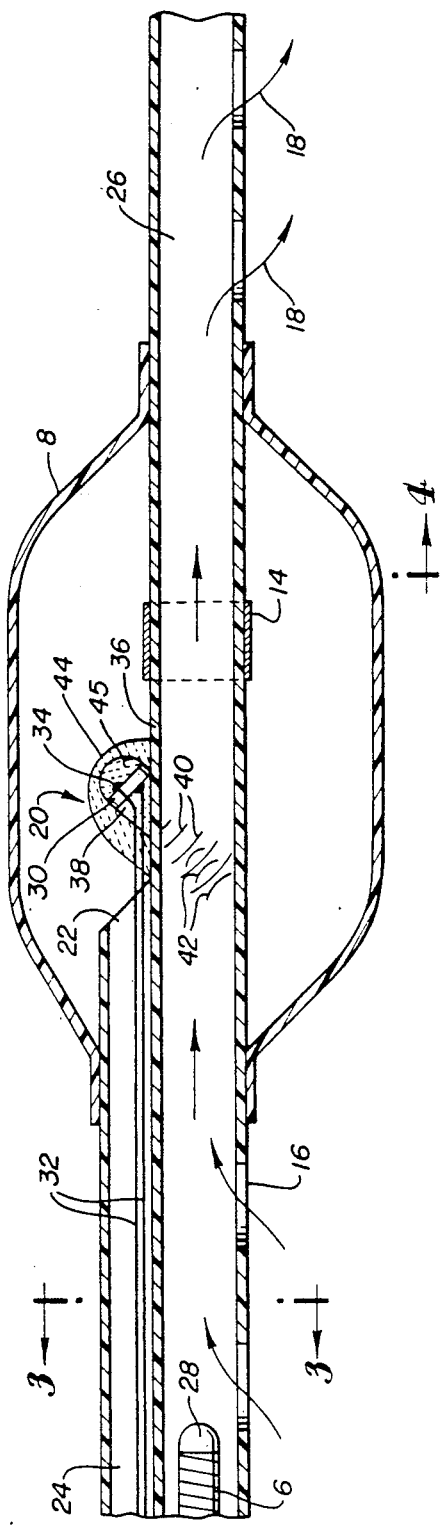

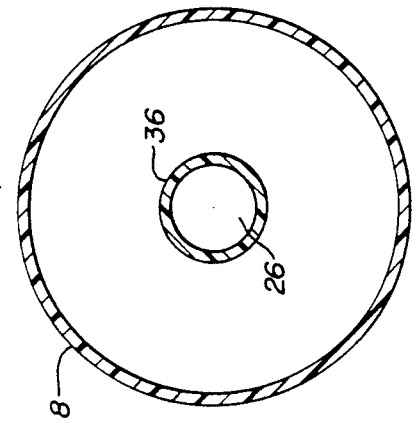
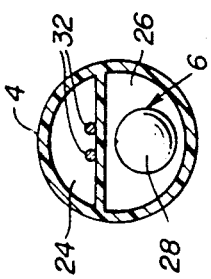
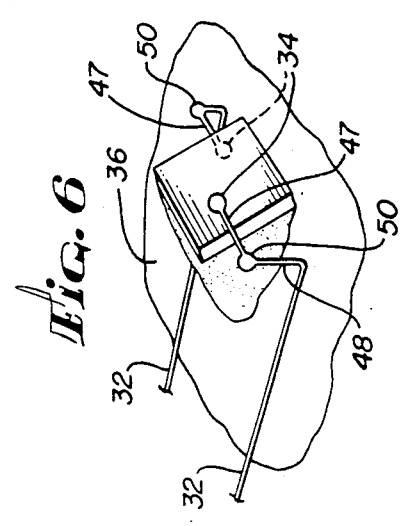
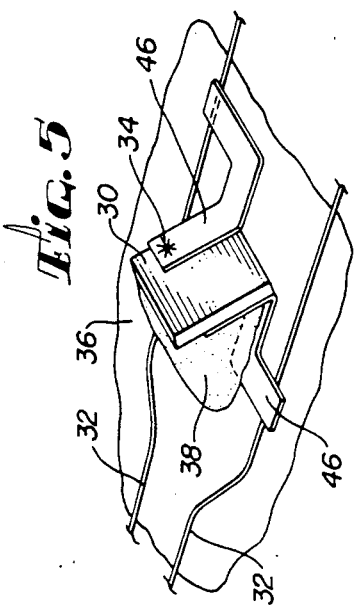
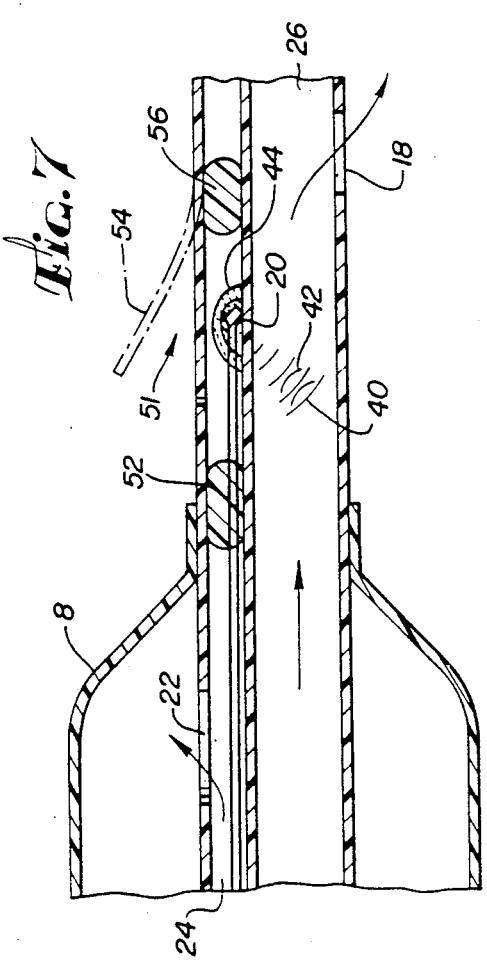

5,046,503

ANGIOPLASTY AUTOPERFUSION CATHETER FLOW MEASUREMENT METHOD AND APPARATUS

BACKGROUND OF THE INVENTION

1. Field of the Invention

This invention relates to the field of intravenous catheters, and more particularly, to balloon angioplasty catheters with autoperfusion and flow measurement capabilities.

2. Description of the Related Art

The use of balloon dilatation angioplasty as an alternative to heart bypass surgery has increased as improved catheter systems and techniques have been developed to advance the probability of success of such non-surgical solutions to blockage in arteries supplying blood for the heart. Balloon angioplasty involves the insertion of a catheter into the area of stenosis in the artery and inflation of a balloon incorporated near the distal tip of the catheter. This procedure provides a means of dilating the plaque on the artery wall, thereby providing a greater area through which blood may flow in the artery. The balloon is usually inflated through a lumen within the catheter by pumping fluid into the lumen from an external source located outside of the body. A common fluid used for this inflation is radiopaque dye.

A variety of techniques and apparatus suitable for balloon angioplasty have been developed and one problem with the basic balloon dilation catheters has been caused by blood stoppage through the artery when the balloon is being inflated. Thus, it is generally necessary to limit the amount of time that the balloon can be inflated in order to limit the possibility of angina or further heart damage. In order to increase the amount of time available for balloon inflation without causing these undesirable side effects, autoperfusion catheter systems have been developed which incorporate a conduit for blood flow past the balloon subsystem in the distal end of the catheter. Such autoperfusion catheters incorporate an entry upstream of the balloon, a lumen within the portion of the catheter incorporating the balloon, an exit to the lumen located near the distal end and downstream of the balloon.

Thus, a passage for the flow of blood is provided to bypass the inflated balloon, thereby providing an opportunity to keep blood flowing to the heart muscle while the balloon is being inflated during the angioplasty procedure.

While such autoperfusion catheters are an improvement over previous non-perfusion catheters, they nonetheless do not guarantee an adequate flow of blood past the balloon since, for example, the small orifices and lumen associated with the bypass of blood may become occluded without an immediate external indication. Flow may also be compromised if the entry or exit holes in the lumen are positioned too close to the artery wall or plaque. Such problems would not easily be detected externally from the body except for the subsequent complaints of chest pain by the patient. Such complaints may be delayed in patients with high pain threshholds and/or by the concomitant use of drugs. Therefore, there is a need for a means of directly and continuously measuring the blood flow in an autoperfusion catheter for use as a monitoring tool to help optimize the autoperfusion feature of the catheter during a balloon dilatation angioplasty procedure. To be effective, such a flow measurement means should be simple, small, easily incorporated in an otherwise standard autoperfusion balloon dilatation angioplasty catheter system and should be amenable to a variety of outputs that could be monitored by the physician performing the angioplasty or an assistant. The measurement should be quantitative or qualitative, the latter providing trend information.

SUMMARY OF THE INVENTION

The purpose of a balloon dilatation angioplasty catheter is to provide a mechanism and apparatus to place and inflate a balloon that is formed integral with the catheter into an area of stenosis in an artery. The placement of the balloon is accomplished by means of remote manipulation of a catheter incorporating the balloon near the distal tip of the catheter, generally by means of sliding the catheter over a guide wire which is manipulated into the appropriate position by a physician after being remotely inserted into an arterial branch of the heart.

After the balloon is properly placed in the area of stenosis, the balloon, located near the distal end of the catheter, is inflated by injecting or pumping a radiopaque dye solution into the lumen communicating between the balloon and a manifold at the proximal end of the catheter located outside of the body. As the balloon is inflated, the stenosis is expanded by the angioplasty catheter. However, if the balloon is left inflated too long, the blood flow to the artery feeding the heart will be blocked for a sufficient time to cause angina or perhaps even damage to the heart muscle. In order to significantly increase the allowable inflation time without causing such damage, autoperfusion catheters have been developed which incorporate a means of moving blood past the inflated balloon through the use of a lumen or channel internal to the catheter and having blood flow orifices communicating with the arterial lumen. The complex nature of such autoperfusion, the possibility of failure or clogging of the autoperfusion channel and the possibility that, for a variety of reasons, the channel may not be providing an adequate flow of blood to prevent angina or heart damage, have combined to indicate that it would be very useful to provide a reliable method to monitor the blood flow rate through the autoperfusion channel.

According to the present invention, a flow measurement system is incorporated in the dilatation catheter to thereby measure the flow of blood through the autoperfusion channel. In one preferred embodiment, the invention utilizes a Doppler sensor placed in a portion of the catheter, adjacent the autoperfusion channel, to allow the direct measurement of blood velocity in the channel. If desired, the volumetric flow may be inferred from the velocity measurement or other calibrated parameters.

The mechanism of the Doppler measurement system incorporates a piezoelectric crystal that is excited with electromagnetic energy of a desired frequency, thereby causing emission of a beam of ultrasound waves into the medium to be measured (e.g., blood flowing through the autoperfusion channel). The waves are reflected back to the crystal at a frequency that is shifted in proportion to the velocity of the medium being measured. The same crystal that is being used to radiate the wave can also be used to detect the reflected wave using well-known pulsed, or continuous wave, Doppler techniques. The crystal is mounted in a portion of the catheter adjacent to the autoperfusion channel and is adhesively bonded to the wall of the channel for acoustically coupling the crystal therethrough. In practice, an appropriate location for the crystal is on the outside of the autoperfusion channel wall inside the balloon. In this way, the measurement device does not need to be in direct physical contact with the blood, and the autoperfusion lumen is not compromised by the presence of the device. The conductors connecting the crystal to the signal generation and readout electronics can be placed within one of the lumens, such as the inflation/deflation lumen, for the balloon.

The entire flow measuring apparatus can be made small enough so that it does not significantly interfere with the primary functions of the catheter system by either significantly altering its external diameter in any critical area, thereby decreasing the flexibility of the catheter, or altering the functioning of the balloon inflation, the guide wire system or autoperfusion channel.

Thus, the present invention provides a means to allow a physician to continuously monitor the blood flow velocity through the autoperfusion channel while the dilatation procedure takes place. A direct indication of the blood flow velocity may be provided to the physician by means of an aural signal in which the amplified sound frequency is proportional to the blood flow velocity, thereby eliminating the necessity for the physician to direct his attention away from the procedure towards a visual read-out of the velocity indication. The velocity may also be displayed to an attending doctor or technician by means of a conventional, digital or analog read-out meter, or on a strip chart recorded or the like.

From the above description, it is clear that the invention can be relatively inexpensive and simple to incorporate into dilatation angioplasty catheters, since the only part of the system which need be incorporated into the disposable catheter is the relatively inexpensive crystal and the necessary wiring. The complex electronics and other read-out systems can be remotely located from the catheter and attached to the catheter system by means of conventional connectors.

It can be readily seen that the present invention provides a simple and inexpensive means of providing a reliable indication to the physician of the blood flow through an autoperfusion lumen in a balloon dilatation catheter incorporating autoperfusion as a feature. The invention thus provides an important and previously unavailable monitoring tool for the physician utilizing dilatation angioplasty catheter systems, since the physician can use the indications provided by the Doppler velocity measurement system to assist in determining the proper functioning and effect of the autoperfusion catheter during an angioplasty procedure.

Other features and advantages of the present invention will become apparent from the following detailed description, taken in conjunction with the accompanying drawings, which illustrate by way of example, the principles of the invention.

BRIEF DESCRIPTION OF THE DRAWINGS

FIG. 1 is a sectioned plan view of the flow sensor of the present invention as it appears in an angioplasty balloon dilitation catheter system incorporating autoperfusion, with the balloon portion shown in cross-section to illustrate placement of the sensor.

FIG. 2 is an enlarged cross-sectional side view of an angioplasty balloon dilatation catheter incorporating the present invention, illustrating one preferred placement of the sensor adjacent to the autoperfusion lumen.

FIG. 3 is a cross-sectional view of the catheter system incorporating the invention taken along line 3—3 of FIG. 2, illustrating the placement of the conductors in the inflation lumen and the guidewire within the autoperfusion lumen.

FIG. 4 is a cross-sectional view of the catheter system taken along line 4—4 of FIG. 2, illustrating the balloon surrounding the central autoperfusion lumen and guidewire.

FIG. 5 is a plan view of a preferred embodiment of the Doppler sensor and the connections between the piezoelectric chip and the conductors.

FIG. 6 is a plan view showing an alternative construction of the connections between the piezoelectric chip of the sensor and the conductors in communication with the sensor.

FIG. 7 is a cross-sectional side view of an alternative construction of the present invention illustrating the sensor placed distally from the balloon and located within a sealed portion of the inflation lumen.

DETAILED DESCRIPTION OF THE PREFERRED EMBODIMENT

A typical autoperfusion balloon dilatation catheter incorporates an autoperfusion channel within the balloon section that is connected to vents in the catheter wall located proximally and distally from the balloon. Thus, when the balloon is inflated to displace the plaque from the central portion of the artery, blood flows through the autoperfusion channel and provides blood flow to the muscle being served by the artery. Unfortunately, previous applications of autoperfusion catheters did not provide an indication of the blood flow through the autoperfusion channel and the physician was forced to rely upon complaints of angina by the patient or other extrinsic indications of diminished blood flow.

The present invention provides a means of directly indicating the flow velocity of blood within the autoperfusion channel and, in the case of a channel with predictable cross sectional characteristics during the procedure, the volumetric blood flow being supplied through the artery can be calculated. The invention is embodied in a velocity sensor located adjacent to the autoperfusion channel and coupled to the channel in such a way that the velocity within the channel may be measured by the sensor. The measured velocity may then be transmitted to a remote location where the velocity or volume flow information may be displayed or otherwise provided to the physician or one of his assistants.

In one embodiment of the invention the sensor incorporates a piezoelectric crystal capable of transmitting sound waves through a coupling medium and the wall of the autoperfusion channel to thereby transmit sound of a predetermined frequency into the fluid flowing through the channel. By using well-known pulse, or continuous wave, Doppler principles and the appropriate choice of frequencies that are interactive with blood, one can determine the velocity of the blood since the frequency of a reflected wave is shifted in proportion to the velocity of the blood flowing through the channel. A frequency of about 20 megahertz (MHz) has been found to work well in this application. The reflected wave is detected by the crystal and is measured by suitable remotely located electronics that translates the measured wave into an indication of the velocity of blood flowing through the channel. The electronics providing this derived indication of velocity can also operate associatively with electronics that provide control of the emission frequency of the crystal and other related functions. Communication between the crystal and the remote electronics is conveniently accomplished by very small wires or other conductors located in a noninterference fashion in one of the lumens of the catheter. Such wires may be conveniently located for instance, within the inflation lumen which is used to inflate and deflate the balloon during the procedure. From the above, it should be appreciated that the present invention represents a substantial improvement in autoperfusion catheter systems, in that it consists of a simple, reliable and accurate means of indicating flow velocity within an autoperfusion channel to a physician performing an angioplasty.

FIG. 1 is a sectioned overall view of an autoperfusion catheter system 2 incorporating the present invention. An outer cover or wall 4 houses a plurality of lumens including one which provides a passageway for a guide wire 6, which during the initial stages of the angioplasty procedure protrudes from the distal end of the catheter 2. A balloon 8 is formed external to and attached to the exterior of outer cover 4 and is inflated through an inflation manifold port 12 located in a manifold 10. A radiopaque collar 14 is provided around the outer covers to give an external indication of the location of the balloon 8 to the physician during the procedure. Autoperfusion inlet ports 16 are provided proximally to the balloon 8 and autoperfusion outlet ports 18 are provided distally from the balloon 8 to provide blood flow past balloon 8 when it is inflated during the procedure. An autoperfusion lumen or channel 26 (shown in detail in FIG. 2) is built into the catheter and acts as a conduit or channel for the blood to flow from the inlet port 16 to the east port 18.

Means for measuring the flow of blood within the autoperfusion channel 26 are shown as a flow sensor 20 located adjacent to and in acoustic communication with the autoperfusion channel 26. The sensor 20 may be conveniently located within the balloon 8 away from the inflation lumen port 22 that is found at the distal end of the inflation lumen 24. Thus, the present invention provides a means for measuring the flow of blood within the autoperfusion lumen without interfering with either the autoperfusion function or any other functions provided by the angioplasty catheter system.

FIG. 2 is an enlarged cross-sectional view taken longitudinally through the balloon and catheter system of FIG. 1. In this view it may be readily seen that the outer cover 4 of catheter 2 encloses the inflation lumen 24 and autoperfusion lumen 26. The inflation lumen 24 is in communication with the inside of balloon 8 through inflation lumen port 22 while autoperfusion lumen 26 acts as an autoperfusion channel between ports 1 6 and outlet ports 18 to thereby bypass the balloon 8 when it is inflated during an angioplasty procedure. As was described above, a radiopaque collar 14 is provided to assist the physician in locating the balloon portion of the catheter system during the angioplasty procedure. During the time that the procedure is being performed, the guidewire 6 is retracted in the autoperfusion lumen 26 until the tip 28 of guidewire 6 is retracted behind the proximal end of autoperfusion inlet ports 16 to thereby provide a clear flow of blood through inlet ports 16 into the autoperfusion channel 26.

As may be seen more clearly in FIG. 2, the flow sensor 20 may consist of a piezoelectric chip or crystal 30 that is connected to an external signal source and measurement electronics (not shown in FIG. 2) through conductors 32 that are spot welded, soldered or attached with conductive adhesive, at connections 34 to the chip. The Doppler chip may be angled to point upstream (as illustrated) or downstream for velocity measuring purposes. The conductors 32 may be placed in inflation lumen 24 without interfering with the inflation process of balloon 8 and the sensor 22 may be placed a distance away from lumen port 24, thereby eliminating interference between the function of port 24 during the inflation or deflation process. The flow sensor 20 may be attached to a wall 36 of autoperfusion lumen 26 by a suitable adhesive 38 to promote ultrasonic transmissions 40 through the wall 36 into the blood flow in the autoperfusion lumen 26. The same flow sensor can be used to receive the reflected waves 42 that bounce off the flowing blood cells. Remote electronics may activate the piezoelectric chip 30 through the conductors 32 to thereby emit the ultrasonic transmissions 40 in the form of waves into the blood flowing through autoperfusion lumen 26 causing a Doppler frequency shift in the reflected wave 42 which again is detected by the piezoelectric chip 30 in the form of signals which can be transmitted through the conductors 32 to a remote location where the signals are processed and recorded. These signals can be derived to provide an indication of the velocity of flow through the lumen. If the cross-sectional area of the autoperfusion lumen can be kept constant in the vicinity of sensor 22, the volumetric flow through the lumen may be derived from this information and displayed to the physician during the procedure.

FIG. 3 is an illustration of the cross section of the catheter system along line 3—3 of FIG. 2, illustrating the guide wire 6 within autoperfusion channel 26 and conductors 32 within inflation lumen 24, all enclosed by the outer cover 4 of the catheter 2. FIG. 4 also shows a cross-sectional view of the catheter system at a location further down along the distal end of the catheter 2. This Figure shows the balloon as it is expanded after inflation during the angioplasty procedure. The autoperfusion lumen 26 is also shown as it houses the guide wire 6.

FIG. 5 is an enlarged detail of the flow sensor 20 illustrating the relationship of piezoelectric chip 30 and one preferred embodiment of connection between the chip 30 and the conductors 32. In this embodiment, connectors 46, made from conductive metal or similar material, are spot welded or soldered to the piezoelectric chip 30 and are also spot welded or soldered to conductors 32 to provide electrical communication with the remote electronics. The conductors 46 may alternatively be formed of conductive epoxy, paint, or ink that may be "painted" in place. Adhesive 38 is provided to adhesively attach the chip 30 to the autoperfusion lumen wall 36 and to maintain the stability betwen the connectors 46 and the chip 30. As is further illustrated in FIG. 2, the backside of the piezoelectric chip may be coated with a sound insulator 45, such as foam or epoxy with hollow beads of glass or the like, to prevent propagation of ultrasound in a direction other than the desired direction. The entire apparatus may be further surrounded by an electrical insulator 44 to provide insulation of the electrical signals from the surrounding inflation liquid medium and other conductors.

FIG. 6 illustrates an alternative embodiment of the flow sensor 20 in which the conductors 32 are directly attached to the connections 34 by small pieces of wire 47 that are soldered between the connections 34 and the ends 48 of conductors 32 with solder or spot welds 50. Alternative means of attaching connectors 34 to the chip 30 include ball bonding and conductive adhesives. The entire assembly may be bonded to autoperfusion lumen wall 36 and surrounded by sound and electrical insulation material 45 and 44 respectively, which also provides a stabilizing overlay to the sensor 20 as was shown in FIGS. 2 and 5.

FIG. 7 illustrates an alternative construction in which the sensor may be mounted away from the balloon 8 in an extended portion of 51 of the inflation lumen 24. In this embodiment, the inflation lumen port 22 is cut in the wall of the inflation lumen 24 and is sealed from the extended portion 51 by a quantity of adhesive such as epoxy 52. The flow sensor 20 is installed by peeling away a portion 54 of the outer cover 4 that is adjacent to the inflation lumen 24. A quantity of adhesive such as epoxy 56 is placed distally from sensor 20 to seal the sensor in the inflation lumen 24 and the flap 54 is later rebonded to the outer cover 4 to seal the assembly. Thus, this configuration provides an equally effective means of coupling the ultrasonic waves emitted by flow sensor 20 into the autoperfusion lumen 26 to thereby measure the velocity of blood flowing therethrough.

The invention has been described in the context of a single Doppler measurement of blood velocity, but those skilled in the art will recognize that various techniques to vary the range gates of the signal may be used to further characterize the flow in the autoperfusion channel. For example, but not by way of limitation, variations in the range gate may be used to characterize the profile of velocities in the autoperfusion channel or detect the presence and location of an obstruction such as a blood clot. Multiple range gate data may be used in combination with an algorithm developed for a given catheter design to allow more accurate measurement of volumetric flow. Alternatively, the Doppler signal may be processed using spectral analysis techniques known in the art. Alternative piezoelectric materials (e.g. PZT ceramic or PVDF polymer) may be used as known in the art.

It is clear that it is also possible to partially recess the sensor within the wall of the autoperfusion lumen by partially notching the outer surface of the wall.

It should be appreciated that other types of flow or velocity measuring devices can be incorporated into the balloon catheter without departing from the spirit and scope of the invention. For example, a hot film anemometer or ultrasound laser measuring device could be used instead of the Doppler crystal. An electromagnetic blood flow measuring device could also be used. Each device would of course have to be adapted for mounting with the autoperfusion lumen to provide accurate measurements.

From the above it may be seen that the present invention represents a simple and elegant solution to the measurement of blood flow through an autoperfusion lumen of the type used during an angioplasty procedure. The placement of such a sensor does not interfere in any significant way with the other functions of the autoperfusion balloon dilatation catheter system and provides an important diagnostic aid to the physician during his use of such catheter systems.

While particular forms of the invention have been illustrated and described, it will also be apparent to those skilled in the art that various modifications can be made without departing from the spirit and scope of the invention. Accordingly, it is not intended that the invention be limited except as by the appended claims.

We claim:

1. An improved autoperfusion angioplasty catheter system of the type incorporating a balloon located near distal tip of the catheter, an autoperfusion lumen within the balloon, and autoperfusion orifices located proximally and distally from said balloon, said orifices providing means to allow the flow of blood through said autoperfusion lumen when said balloon is inflated, said improvement comprising:

measurement means located adjacent said autoperfusion lumen and in communication therewith for measuring the flow of blood through said autoperfusion lumen;

means to activate said measurement means from a remote location; and indication means to provide at said remote location an indication of flow movement as measured by said measurement means.

2. The improved autoperfusion catheter system of claim 1 wherein said measurement means comprises velocity measurement means.

3. The improved autoperfusion catheter system of claim 2 wherein said velocity measurement means further comprises Doppler velocity measurement means.

4. The improved autoperfusion catheter system of claim 3 wherein said Doppler velocity measurement means further comprises:

a transducer located adjacent to and in communication with said autoperfusion lumen thereby acoustic coupling through the wall of said lumen;

means to excite said transducer to thereby cause said transducer to emit ultrasonic waves of a predetermined frequency into blood flowing in said autoperfusion lumen; and means to detect a shift in frequency between said emitted ultrasonic waves and reflected ultrasonic waves received by said transducer.

5. The improved autoperfusion catheter system of claim 4 wherein said means to electrically activate said Doppler measurement means from a remote location includes an electronic signal generator.

6. The improved autoperfusion catheter system of claim 6 wherein said means to electrically activate said Doppler measurement means from a remote location further comprises electrical conductors connected to said Doppler velocity measurement means and placed within a lumen of said catheter system.

7. The improved autoperfusion catheter system of claim 1 wherein said measurement means is located within said balloon.

8. The improved autoperfusion catheter system of claim 1 wherein said means to provide at a remote location an indication of flow movement further comprises means to visually display said flow movement.

9. The improved autoperfusion catheter system of claim 1 wherein said means to provide at a remote location an indication of flow movement further comprises means to audibly indicate said flow movement.

10. In an autoperfusion catheter of the type that incorporates an inflatable balloon near the distal end of the catheter, an autoperfusion lumen internal to said balloon, autoperfusion vents placed proximally and distally from said balloon, said vents in communication with said autoperfusion lumen and the exterior of said catheter to provide a passage for blood past said balloon when it is inflated, an improvement which comprises:

flow measurement means located adjacent and in communication with said autoperfusion lumen;

means to communicate between said flow measurement means and a remote location;

control means at said remote location whereby said flow measurement means may be activated and measurement of flow to said autoperfusion lumen may be received; and indicator means at said remote location whereby an indication of said flow measurement may be provided.

11. The improved autoperfusion catheter system of claim 10 wherein said flow measurement means further comprises velocity measurement means.

12. The improved autoperfusion catheter system of claim 11 wherein said velocity measurement means is located within said balloon.

13. The improved autoperfusion catheter system of claim 11 wherein said velocity measurement means comprises Doppler velocity measurement means.

14. The improved autoperfusion catheter system of claim 13 wherein said Doppler velocity measurement means further comprises:

a transducer of piezoelectric material located adjacent to and in communication with said autoperfusion lumen;

means to excite said transducer to thereby cause said transducer to emit ultrasonic waves of a predetermined frequency; and means to detect a shift in frequency between said emitted ultrasonic waves and reflected ultrasonic waves reflected by blood moving in said autoperfusion lumen and received by said transducer.

15. The improved autoperfusion catheter system of claim 14 wherein said means to electrically activate said Doppler measurement means from a remote location comprises an electronic signal generator.

16. The improved autoperfusion catheter system of claim 15 which further comprises means at said remote location to provide an indication of flow velocity as measured by said Doppler measurement means.

17. The improved autoperfusion catheter system of claim 14 wherein said means to electrically activate said Doppler measurement means from a remote location further comprises electrical conductors connected to said Doppler velocity measurement means and placed within a lumen of said catheter system.

18. An improved autoperfusion catheter of the type that incorporates an inflatable balloon means near the distal end of said catheter, an autoperfusion lumen, autoperfusion vents placed proximally and distally from said balloon, said vents providing means to allow the flow of blood in said autoperfusion lumen when said balloon is inflated, wherein said improvement comprises:

flow measurement means located adjacent to and in communication with said autperfusion lumen for measuring the flow of blood through the autoperfusion lumen.

19. The autoperfusion catheter system of claim 18 which further comprises means to activate said flow measurement means.

20. The improved autoperfusion catheter system of claim 18 wherein said flow measurement means further comprises means to detect velocity by sensing changes in electrical resistance of means in contact with said flow of blood.

21. The improved autoperfusion catheter system of claim 18 in which said flow measurement means further comprises means to measure said blood flow by optical velocity detection means.

22. The autoperfusion catheter system of claim 18 in which said flow measurement means further comprises Doppler velocity measurement means.

23. The improved autoperfusion catheter system of claim 22 wherein said Doppler velocity measurement means further comprises:

a transducer of piezoelectric material located adjacent to and in communication with said autoperfusion lumen;

means to excite said transducer to thereby cause said transducer to emit ultrasonic waves of a predetermined frequency; and means to detect a shift in frequency between said emitted ultrasonic waves and reflected ultrasonic waves reflected by blood moving in said autoperfusion lumen and received by said transducer.

24. The improved autoperfusion catheter system of claim 22 wherein said velocity measurement means is located within said balloon.

25. The improved autoperfusion catheter system of claim 22 wherein said means to excite said Doppler measurement means comprises an electronic signal generator.

26. An improved autoperfusion catheter of the type that incorporates an inflatable balloon means near the distal end of said catheter, an autoperfusion lumen, autoperfusion vents placed proximally and distally from said balloon, said vents providing means to allow the flow of blood in said autoperfusion lumen when said balloon is inflated, wherein said improvement comprises:

flow measurement means located adjacent to and in communication with said autperfusion lumen; and means to provide an indication of velocity in said autoperfusion lumen measured by said flow measurement means.

* * * * *